(12) United States Patent
Kandemir

(10) Patent No.: US 9,839,501 B2
(45) Date of Patent: Dec. 12, 2017

(54) MECHANICAL TOOTHBRUSH

(71) Applicant: Alexander Kandemir, New York, NY (US)

(72) Inventor: Alexander Kandemir, New York, NY (US)

( * ) Notice: Subject to any disclaimer, the term of this patent is extended or adjusted under 35 U.S.C. 154(b) by 673 days.

(21) Appl. No.: 14/459,882

(22) Filed: Aug. 14, 2014

(65) Prior Publication Data

US 2015/0147727 A1    May 28, 2015

Related U.S. Application Data

(60) Provisional application No. 61/909,443, filed on Nov. 27, 2013.

(51) Int. Cl.
| | |
|---|---|
| *A46B 15/00* | (2006.01) |
| *A61C 17/26* | (2006.01) |
| *A46B 13/00* | (2006.01) |
| *A61C 17/22* | (2006.01) |
| *A61C 17/34* | (2006.01) |

(52) U.S. Cl.
CPC ............ *A61C 17/26* (2013.01); *A46B 13/003* (2013.01); *A46B 15/0004* (2013.01); *A61C 17/221* (2013.01); *A61C 17/3418* (2013.01)

(58) Field of Classification Search
CPC .......................... A46B 15/0004; A61C 17/26
See application file for complete search history.

(56) References Cited

U.S. PATENT DOCUMENTS

| | | | |
|---|---|---|---|
| 2,628,377 A * | 2/1953 | Cockriel | A61C 17/228 15/167.1 |
| 3,152,272 A | 10/1964 | Hovhanesian et al. | |
| 3,159,859 A | 12/1964 | Rasmussen | |
| 3,405,710 A | 10/1968 | Kovach | |
| 3,451,086 A * | 6/1969 | Burgett | A61C 17/26 119/609 |
| 3,546,501 A | 12/1970 | Kircher | |
| 3,739,416 A † | 6/1973 | Kurachi | |
| 4,163,300 A † | 8/1979 | Quint | |
| 4,320,774 A † | 3/1982 | Rogers | |
| 4,344,202 A † | 8/1982 | Hayat | |
| 4,397,055 A * | 8/1983 | Cuchiara | A61C 17/26 15/22.1 |

(Continued)

FOREIGN PATENT DOCUMENTS

| | | |
|---|---|---|
| JP | 2006-025311 | 2/2006 |
| JP | 2007-202798 A † | 8/2007 |

(Continued)

*Primary Examiner* — Randall Chin
(74) *Attorney, Agent, or Firm* — Michael J. Feigin, Esq.; Feigin & Fridman

(57) ABSTRACT

A mechanical toothbrush, including a housing portion extending along a longitudinal axis, a bristle shaft assembly including a shaft portion disposed within the housing and extending along the longitudinal axis, and a head portion disposed outside of the housing and having a plurality of bristles extending perpendicularly to the longitudinal axis around a circumference of the shaft portion, and an electronic controlling mechanism disposed within the housing portion, the electronic controlling mechanism activating the bristle shaft assembly to rotate about the longitudinal axis.

12 Claims, 7 Drawing Sheets

(56) References Cited

U.S. PATENT DOCUMENTS

| | | | |
|---|---|---|---|
| 4,709,438 A † | 12/1987 | De Tavares | |
| 4,845,796 A * | 7/1989 | Mosley | A61C 17/26 15/105 |
| 5,077,855 A | 1/1992 | Ambasz | |
| 5,235,716 A * | 8/1993 | Stella | A46B 7/04 15/23 |
| 5,699,575 A * | 12/1997 | Peifer | A61C 17/222 15/23 |
| 5,794,296 A * | 8/1998 | Wong | A61C 17/221 15/22.1 |
| 6,347,425 B1 | 2/2002 | Fattori et al. | |
| 6,453,498 B1 | 9/2002 | Wu | |
| 6,701,565 B2 | 3/2004 | Hafemann | |
| 7,464,430 B2 | 12/2008 | Filsouf | |
| 7,784,138 B2 | 8/2010 | Spooner | |
| 8,079,106 B2 † | 12/2011 | Yang | |
| 8,966,695 B1 * | 3/2015 | Bornemann | A46B 7/10 15/22.1 |
| D743,173 S † | 11/2015 | Sohn | |
| 2006/0021166 A1 * | 2/2006 | Hills | A46B 13/005 15/23 |
| 2010/0043157 A1 | 2/2010 | Jungnickel et al. | |
| 2010/0175207 A1 | 7/2010 | Kraus et al. | |
| 2012/0174938 A1 | 7/2012 | Hill | |

FOREIGN PATENT DOCUMENTS

| | | | |
|---|---|---|---|
| KR | 1020040080616 A † | 4/2005 | |
| KR | 10-2010-0018117 | 2/2010 | |
| KR | 1020100018117 A † | 2/2011 | |
| WO | WO 94/3123 | 8/1992 | |

\* cited by examiner
† cited by third party

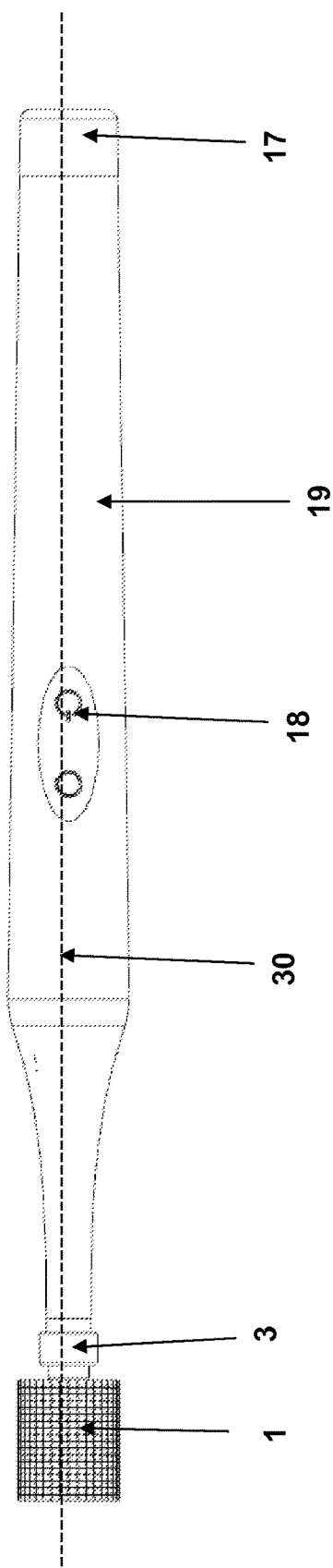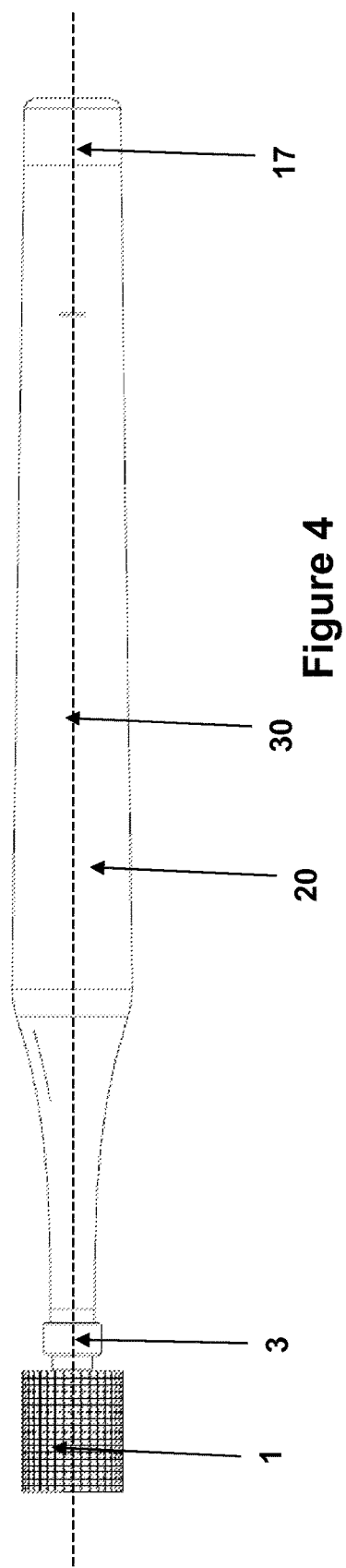

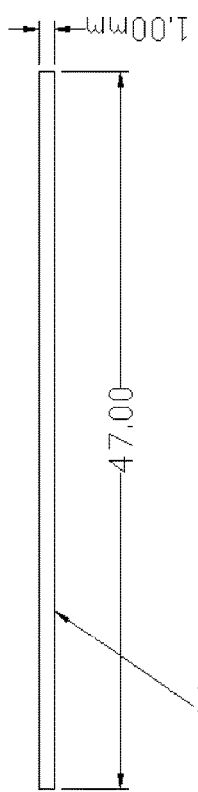
Figure 7
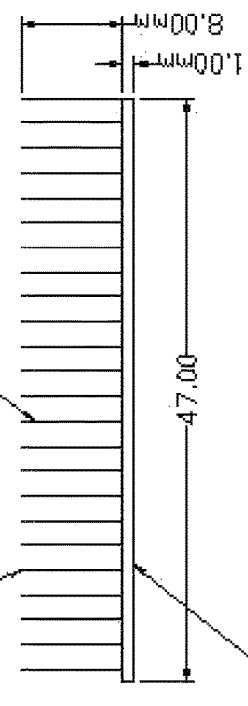
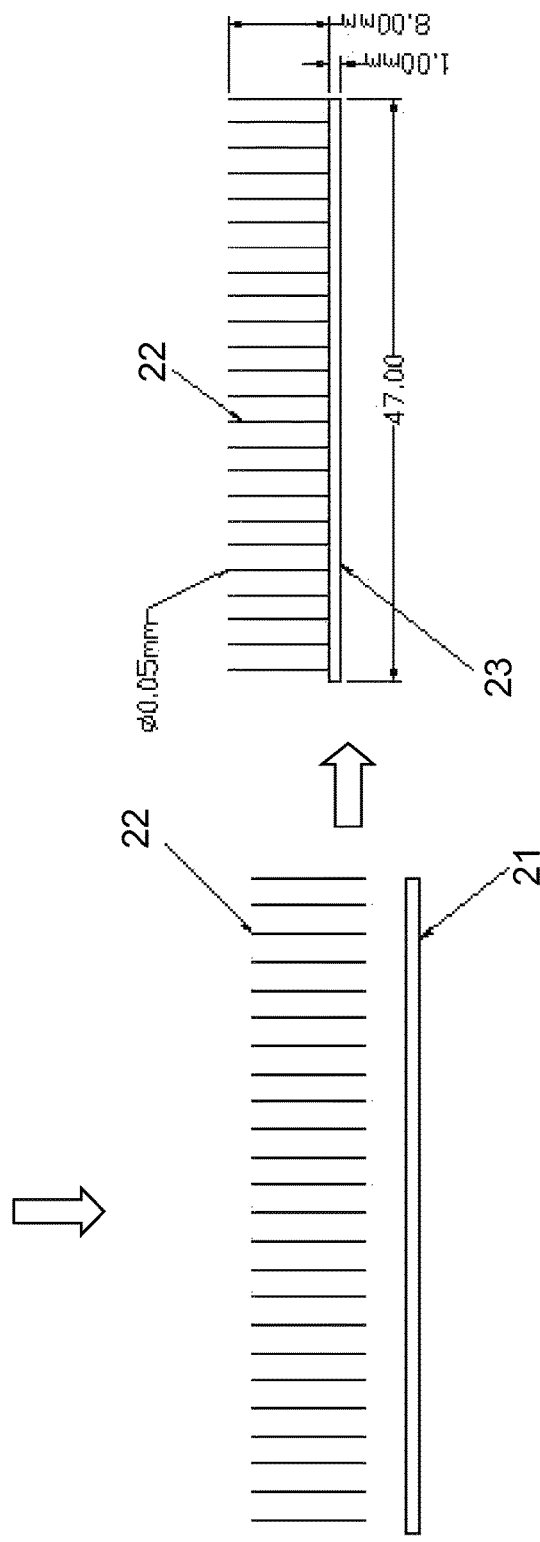
Figure 8
Figure 9

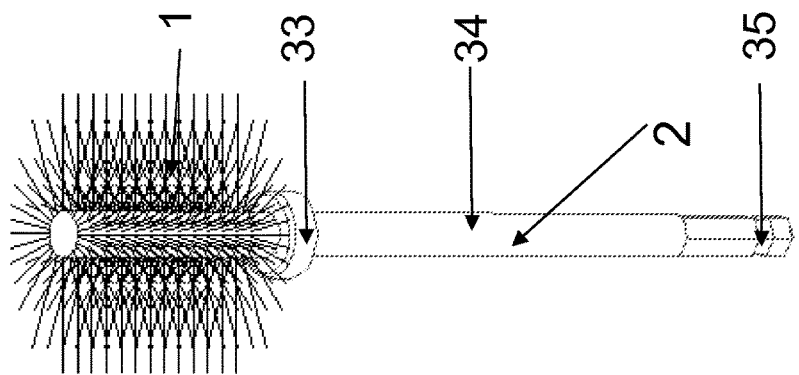
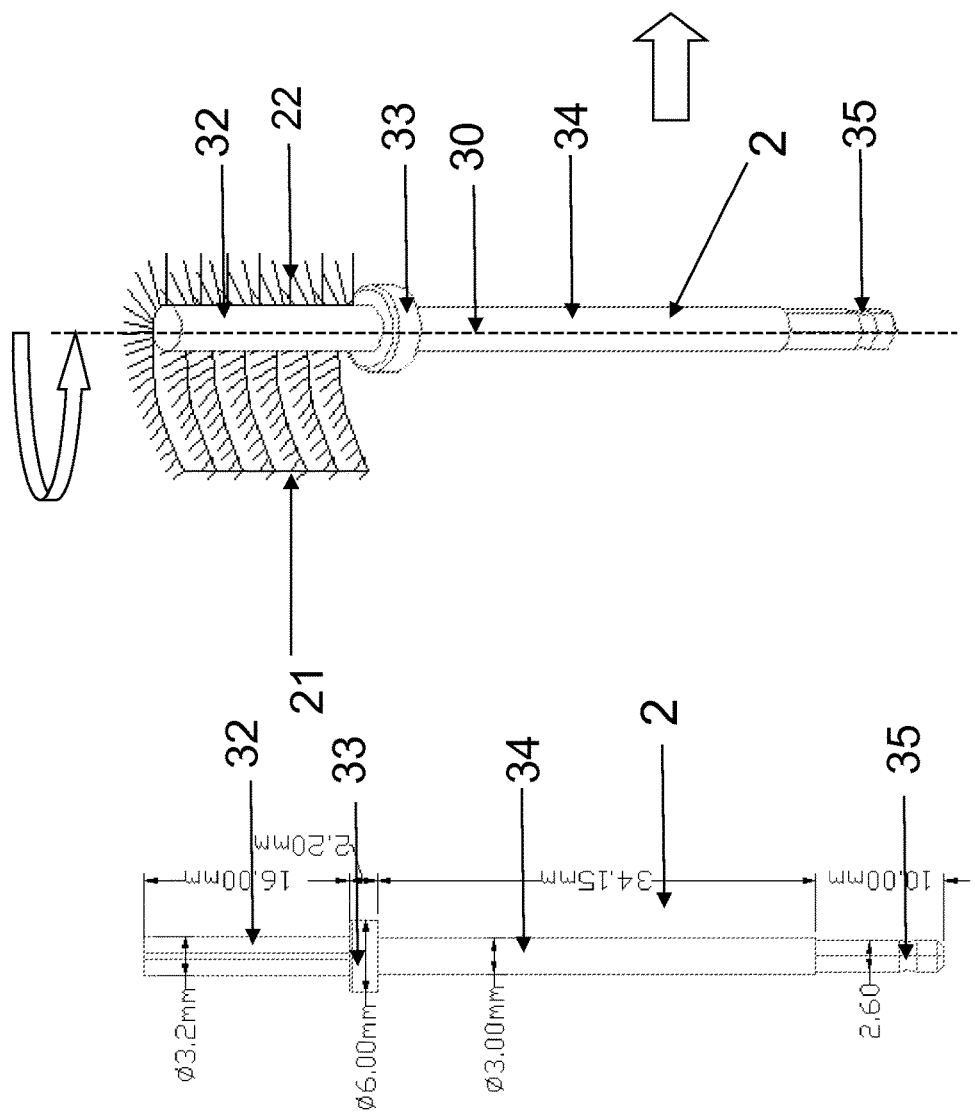
Figure 10
Figure 11
Figure 12

MECHANICAL TOOTHBRUSH

FIELD OF THE DISCLOSED TECHNOLOGY

The disclosed technology relates generally to oral health and hygiene and, more specifically, to a mechanical toothbrush with an orbiting neck, such that the bristles rotate 360 degrees about the neck of the toothbrush.

BACKGROUND OF THE DISCLOSED TECHNOLOGY

For many years, dentists have been advising people to brush their teeth from the gums toward the tooth, by using a rotational up-and-down motion of the wrist. However, the motion is difficult to learn, particularly when the habit of brushing teeth horizontally back-and-forth is commonly ingrained in people and is very hard to break, by brushing their teeth using a horizontal back-and-forth motion, people often push some bacteria into the gums, resulting in gum disease and gingivitis.

A multitude of mechanical toothbrushes is available on the market. Each toothbrush offers a different mechanism for improving the dental hygiene of its users. The most common types of mechanical toothbrushes offer a rotating, vibrating, or reciprocating head. However, due to the fact that only the head of the toothbrush moves, most people continue to use horizontal back-and-forth movements with such mechanical toothbrushes, and continue to introduce bacteria into the gums. Proper and effective use of such mechanical toothbrushes still requires the user to proceed with a rotational motion of the wrist, and not a horizontal back-and-forth movement, and thus requires breaking existing tooth-brushing habits.

Therefore, there exists a need in the art for a toothbrush with bristles which rotate about a longitudinal axis of the toothbrush for mechanically replicating the desired circular motion of a user's hand in properly brushing his/her teeth, without requiring the user to change his or her toothbrushing habits.

SUMMARY OF THE DISCLOSED TECHNOLOGY

The disclosed technology relates generally to oral health and hygiene and, more specifically, to a mechanical toothbrush with an orbiting neck, such that the bristles rotate 360 degrees about the neck of the toothbrush.

According to an aspect of some embodiments of the teachings herein, there is provided a mechanical toothbrush, including
  a) a housing portion extending along a longitudinal axis,
  b) a bristle shaft assembly, including a shaft portion disposed within the housing and extending along the longitudinal axis,
  (c) a head portion disposed outside of the housing and having a plurality of bristles extending perpendicularly to the longitudinal axis around a circumference of the shaft portion, and
  d) an electronic controlling mechanism disposed within the housing portion, the electronic controlling mechanism activating the bristle shaft assembly to rotate about the longitudinal axis.

In some embodiments, the electronic controlling mechanism includes a direction switch, wherein operation of the direction switch changes the direction of rotation of the bristle shaft assembly about the longitudinal axis from a first direction of rotation to a second, opposite direction of rotation.

In some embodiments, the electronic controlling mechanism includes an activation switch, wherein operation of the activation switch activates or stops rotation of the bristle shaft assembly. In some such embodiments, operation of the activation switch changes the speed of rotation of the bristle shaft assembly from a first speed of rotation to a second speed of rotation, faster than the first speed of rotation.

In some embodiments, the head portion comprises a base sheet with, mounted thereon, the plurality of bristles, the base sheet being disposed circumferentially about the shaft portion. In some such embodiments, the plurality of bristles is ultrasonically welded onto the base sheet.

In some embodiments, each of the plurality of bristles has a circumference of less than 0.1 mm. In some such embodiments, each of the plurality of bristles has a circumference in the range of 0.04 mm to 0.07 mm.

According to an aspect of some embodiments of the teachings herein, there is also provided a method for brushing teeth, including in a user's hand, holding the mechanical toothbrush described hereinabove with the head portion against the user's teeth, such that the longitudinal axis lies parallel to the gum-line of the user's teeth, operating an activation switch of the toothbrush to activate rotation of the head portion about the longitudinal axis at a desired one of a first speed of rotation and a second speed of rotation, and operating a direction switch of the toothbrush to select a direction of rotation of the head portion, such that the bristles rotate away from the gum-line and towards ends of the teeth of the user.

In some embodiments, operating a direction switch comprises, when brushing the user's upper teeth, operating the direction switch, so that the bristles rotate downward relative to the user's teeth. In some embodiments, operating a direction switch comprises, when brushing the user's lower teeth, operating the direction switch, so that the bristles rotate upward relative to the user's teeth.

BRIEF DESCRIPTION OF THE DRAWINGS

FIG. 3 shows a top plan view of a toothbrush, according to an embodiment of the disclosed technology.

FIG. 4 shows a bottom plan view of a toothbrush, according to an embodiment of the disclosed technology.

FIGS. 7, 8, and 9 show, in a side plan view, steps of construction of the bristles forming part of a bristle head of a toothbrush, according to an embodiment of the disclosed technology.

FIG. 10 shows a side plan view of a bristle shaft forming part of a toothbrush, according to an embodiment of the disclosed technology.

FIG. 11 shows the construction of the bristles of FIG. 9 onto the bristle shaft of FIG. 10, thereby creating a bristle shaft assembly forming part of a toothbrush, according to an embodiment of the disclosed technology.

FIG. 12 shows a side plan view of a bristle shaft assembly, constructed as shown in FIG. 11, forming part of a toothbrush, according to an embodiment of the disclosed technology.

DETAILED DESCRIPTION OF EMBODIMENTS OF THE DISCLOSED TECHNOLOGY

In an embodiment of the disclosed technology, a toothbrush has an orbiting head and neck, such that the bristles rotate 360 degrees about the neck of the toothbrush. A gear coupled to a drive wheel causes the head of the toothbrush to orbit in a circular motion. When horizontally disposed near teeth, the head is caused to move in a circular and/or orbiting motion towards and away from the teeth, thereby mimicking the movement of a user's wrist in brushing one's teeth.

According to an aspect of some embodiments of the teachings herein, there is provided a mechanical toothbrush, including a housing portion extending along a longitudinal axis; a bristle shaft assembly, including a shaft portion disposed within the housing and extending along the longitudinal axis; and a head portion disposed outside of the housing, and having a plurality of bristles extending perpendicularly to the longitudinal axis around a circumference of the shaft portion; and an electronic controlling mechanism disposed within the housing portion, the electronic controlling mechanism activating the bristle shaft assembly to rotate about the longitudinal axis.

Embodiments of the disclosed technology will become clearer in view of the following description of the drawings.

Figure 1:
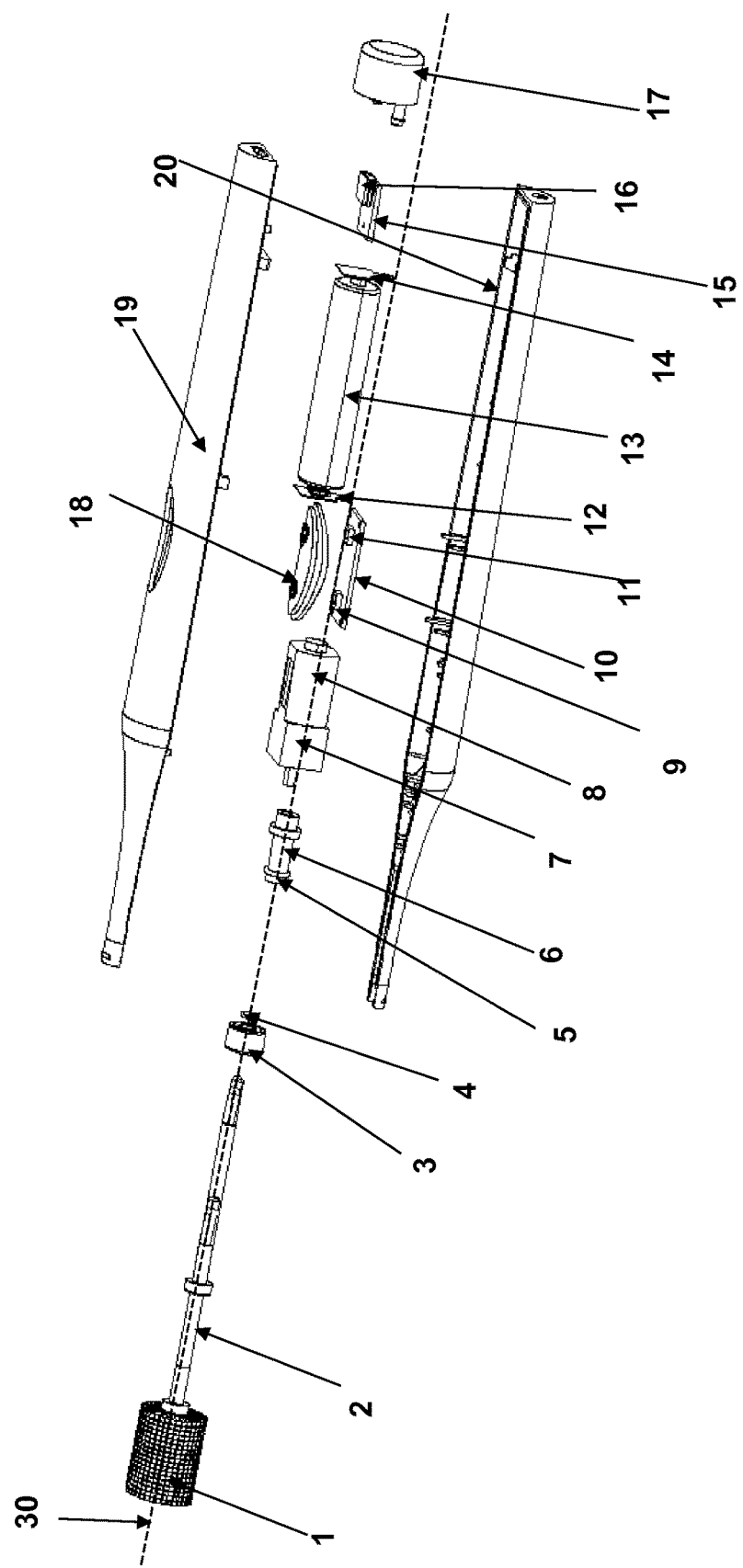
FIG. 1 shows a blown apart view of a toothbrush, according to an embodiment of the disclosed technology.
Figure 2:
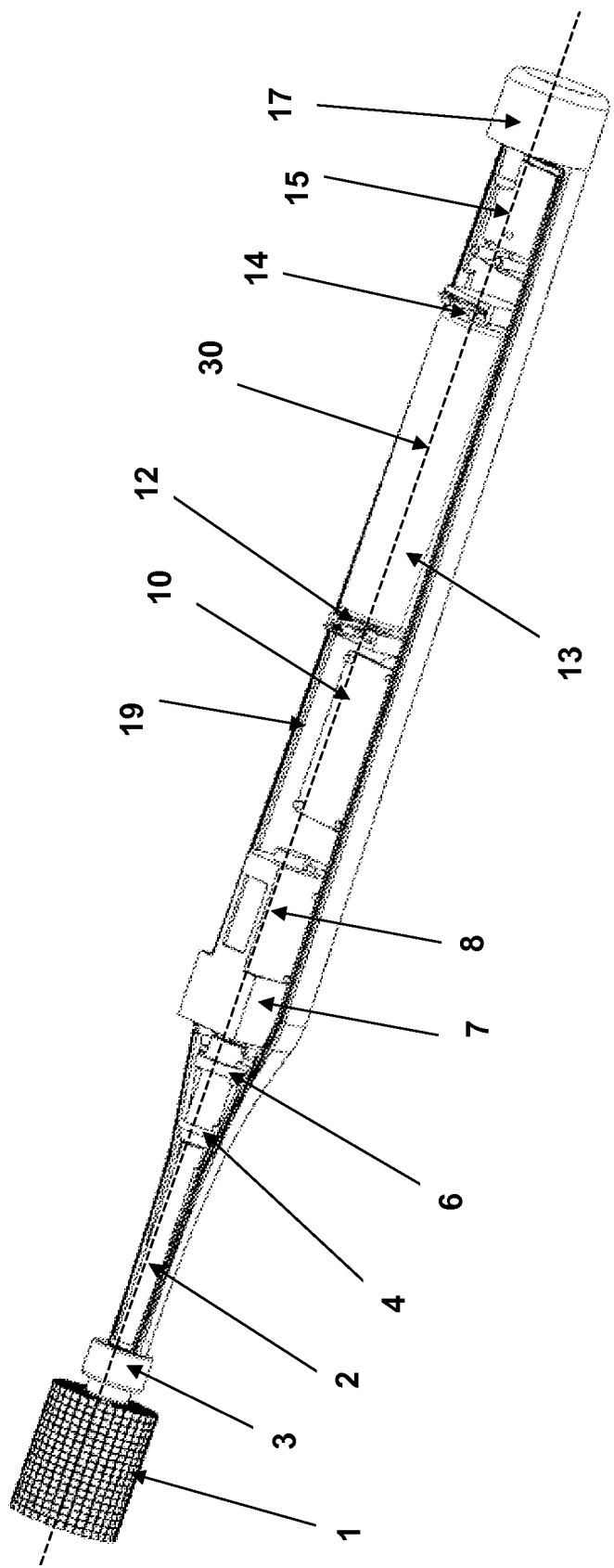
FIG. 2 shows a cut away view of an interior of a toothbrush handle, according to an embodiment of the disclosed technology.

Reference is now made to FIG. 1, which shows a blown apart view of a toothbrush, according to an embodiment of the disclosed technology, and to FIG. 2, which shows a cut-away view of an interior of a toothbrush handle, according to an embodiment of the disclosed technology. As seen, a bristle shaft 2 extends along a longitudinal axis 30 of the toothbrush, and terminates at a proximal portion thereof in a bristle head 1, having bristles formed at 360 degrees around the entirety of the circumference of bristle shaft 2, thereby defining a bristle shaft assembly, as described in further detail hereinbelow with respect to FIGS. 9 to 11.

Bristle shaft 2 is connected to a geared spur box 7 via a connector 3 and an O-ring 4 mounted at the distal end of the shaft 2, and via an O-ring 5 and a connector 6 which connect to a geared spur box 7. The geared spur box 7 is connected to a motor 8, which, in use, drives the rotation of bristle head 1, as described hereinbelow. Motor 8 is coupled to a printed circuit board (PCB) 10, including an activation switch 9 and a direction switch 11.

Motor 8 and PCB 10 are also coupled to, and powered by, a rechargeable battery 13 held between battery electric plates 12 and 14. Electrically coupled to battery 13 is a power transformer 15, connected to a USB (Universal Serial Bus) 16 for connection of the toothbrush to an external power source for recharging of battery 13.

Figure 5:
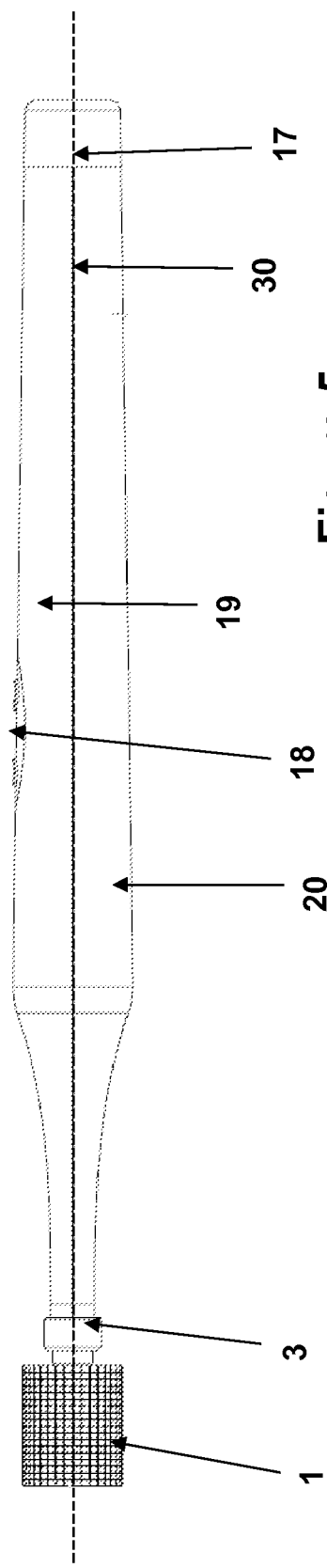
FIG. 5 shows a side plan view of a toothbrush, according to an embodiment of the disclosed technology.

Reference is now additionally made to FIG. 3, which shows a top plan view of a toothbrush, according to an embodiment of the disclosed technology; to FIG. 4, which shows a bottom plan view of a toothbrush, according to an embodiment of the disclosed technology; and to FIG. 5, which shows a side plan view of a toothbrush, according to an embodiment of the disclosed technology.

As seen, the components of the toothbrush, other than bristle head 1 and connector 3, are enclosed in a housing having an upper portion 19 and a lower portion 20. FIG. 5 illustrates the various components housed in lower portion 20 of the housing. Housing portions 19 and 20 may be connected to one another, using any suitable connection method, such as snap fitting, adhering, welding, soldering, and the like. The housing is sealed at a distal end thereof by a waterproof cover 17, allowing access to USB 16 for charging of battery 13. A switch cover 18, which in some embodiments is formed of silicone, is disposed within upper portion 19 of the housing, and is aligned to lie above PCB 10 and switches 9 and 11.

Figure 6:
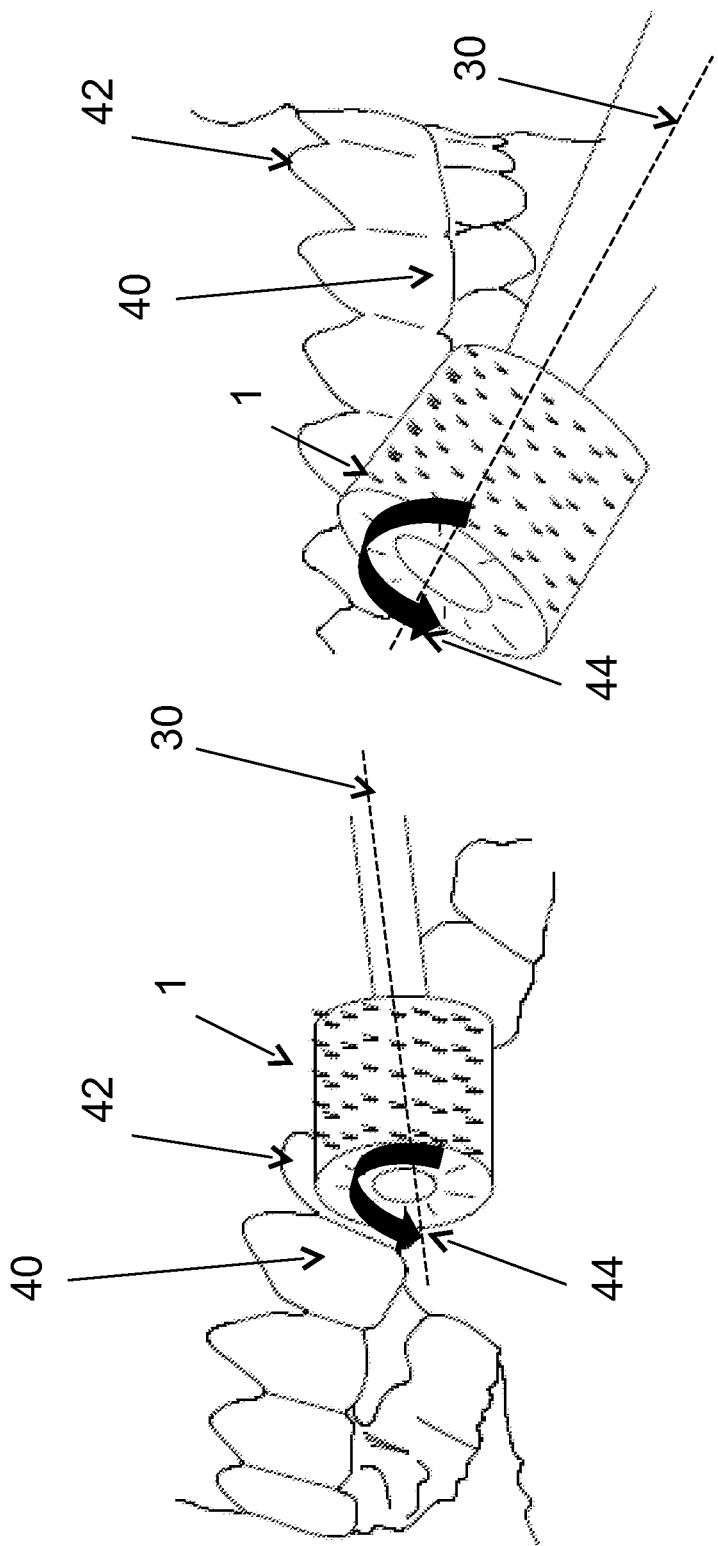
FIGS. 6A and 6B show schematic illustrations of a method of using a toothbrush according to the disclosed technology to brush teeth.

Reference is additionally made to FIGS. 6A and 6B, which show schematic illustrations of a method of using a toothbrush according to the disclosed technology to brush teeth.

In a method of use, a user holds the housing of the toothbrush with bristle head 1 resting against the teeth 40, such that the longitudinal axis 30 lies, generally horizontally, at a sharp angle relative to, or even parallel to, the gum line 42. As seen by comparison of FIGS. 6A and 6B, the exact angle at which the toothbrush is held depends on the teeth being brushed and/or on the comfort of the user. For example, when the mouth is open, as shown in FIG. 6A, the user holds the toothbrush at a different angle than when the mouth is closed, as shown in FIG. 6B.

Depression of activation switch 9 activates the toothbrush at a first bristle rotation speed, additional depression of activation switch 9 changes the bristle rotation speed to a second bristle rotation speed, faster than the first bristle rotation speed, and yet further depression of activation switch 9 causes deactivation, or turning off, of the toothbrush. Thus, the user may use activation switch 9 to determine the desired speed of rotation, based on his or her comfort level.

Depression of direction switch 11, while the toothbrush is operative, changes the direction of the bristle head rotation 1. For example, if bristle head 1 is rotating clockwise relative to longitudinal axis 30, depression of direction switch 11 causes the bristle head 11 to rotate counter-clockwise relative to longitudinal axis 30. By using the direction switch 11, the user may ensure that the bristles are rotating from the gum line towards the teeth, as indicated by arrow 44 in FIGS. 6A and 6B, such that the motion of the bristles pulls plaque and buildup away from the gums regardless of whether the toothbrush is used on the upper or lower teeth. Thus, when brushing the upper teeth, the user depresses the direction switch 11 to ensure that the bristles are rotating from the top downwards, in a first direction, shown by arrow 44. Conversely, when brushing the lower teeth, the user depresses the direction switch 11 to ensure that the bristles are rotating from the bottom upwards, in the opposite direction.

Reference is now made to FIGS. 7, 8, and 9, which show in a side plan view steps of construction of the bristles forming part of a bristle head of a toothbrush, according to an embodiment of the disclosed technology. Specifically, FIG. 7 shows a side plan view of a substantially planar flexible base sheet 21, which is used as a base for the bristles of the bristle head 1. Base sheet 21 may be fabricated of any suitable material, though, in some embodiments, it is fabricated of flexible nylon. In some embodiments, the thickness of base sheet 21 is not greater than 1 mm. FIGS. 8 and 9 illustrate the connection of bristles 22 perpendicularly to the plane of base sheet 21. Bristles 22 may be connected to base sheet 21 in any suitable manner, though, in some embodiments, the bristles 22 are ultrasonically welded to the base sheet 21. In some embodiments, the diameter of each bristle is in the range of 0.1 mm to 0.01 mm, and, in some embodiments, is 0.05 mm. In some embodiments, the length of each bristle is in the range of 5 mm to 10 mm, and in some embodiments is 8 mm. The number of bristles 22 connected to the base sheet 21 is dependent on the dimensions of the base sheet 21. However, in some embodiments, more than 10,000 bristles, more than 12,000 bristles, more than 15,000 bristles, or more than 18,000 bristles are used on a single base sheet 21.

Reference is now made to FIG. 10, which shows a side plan view of bristle shaft 2 forming part of a toothbrush, according to an embodiment of the disclosed technology; to FIG. 11, which shows the construction of the bristles 22 of FIG. 8 onto bristle shaft 2 of FIG. 10, thereby creating a bristle shaft assembly forming part of a toothbrush, according to an embodiment of the disclosed technology; and to FIG. 12, which shows a side plan view of a bristle shaft assembly, constructed as shown in FIG. 11, forming part of a toothbrush, according to an embodiment of the disclosed technology.

As seen in FIG. 10, bristles shaft 2 includes at a proximal portion thereof a top portion 32, having a first diameter, onto which the bristles are mounted. In some embodiments, the diameter of the top portion is slightly larger than 3 mm, and, in some embodiments, is 3.2 mm. A flange 33, having a diameter greater than the first diameter of top portion 32, is located distally to the top portion. In some embodiments, the diameter of flange 33 is approximately double the diameter of the top portion 32, and in some embodiments is 6 mm. A shaft portion 34 is disposed distally of flange 33, and, in some embodiments, has a diameter slightly smaller than the first diameter of top portion 32, and, in some embodiments, has a diameter of 3 mm. A connector portion 35, located at the distal end of bristles shaft 2, is constructed to be coupled to geared spur box 7 and to be driven thereby; in some embodiments has a diameter slightly smaller than that of shaft 34; and in some embodiments a diameter of 2.6 mm.

As seen in FIG. 11, base sheet 21 is rotated about top portion 32 of bristles shaft 2, such that the entire circumference of top portion 32 is covered in base sheet 21 and in bristles 22. As seen in FIG. 12, in the bristle shaft assembly, the bristles 22 of bristle head 1 extend perpendicularly to longitudinal axis 30, about the entire circumference of top portion 32.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

The invention claimed is:

1. A mechanical toothbrush, comprising:
   a housing portion extending along a longitudinal axis;
   a bristle shaft assembly including a shaft portion disposed within said housing and extending along said longitudinal axis, and a head portion disposed outside of said housing, and having a plurality of bristles extending perpendicularly to said longitudinal axis around a circumference of said shaft portion; and
   an electronic controlling mechanism disposed within said housing portion, said electronic controlling mechanism activating said bristle shaft assembly to rotate about said longitudinal axis
   wherein said head portion comprises a base sheet having mounted thereon said plurality of bristles, said base sheet being disposed circumferentially about said shaft portion.

2. The mechanical toothbrush of claim 1, wherein said electronic controlling mechanism includes a direction switch, wherein operation of said direction switch changes the direction of rotation of said bristle shaft assembly about said longitudinal axis from a first direction of rotation to a second, opposite direction of rotation.

3. The mechanical toothbrush of claim 1, wherein said electronic controlling mechanism includes an activation switch, wherein operation of said activation switch activates or stops rotation of said bristle shaft assembly.

4. The mechanical toothbrush of claim 3, wherein operation of said activation switch changes the speed of rotation of said bristle shaft assembly from a first speed of rotation to a second speed of rotation, faster than the first speed of rotation.

5. The mechanical toothbrush of claim 1, wherein said plurality of bristles is ultrasonically welded onto said base sheet.

6. The mechanical toothbrush of claim 1, wherein each of said plurality of bristles has a circumference of less than 0.1 mm.

7. The mechanical toothbrush of claim 6, wherein each of said plurality of bristles has a circumference in the range of 0.04 mm to 0.07 mm.

8. An electric toothbrush, comprising:
   a housing extending along a longitudinal axis;
   a bristle shaft assembly comprising a shaft part disposed inside the housing and extending along the longitudinal axis and a head part disposed outside the housing and having multiple bristles that extend around the shaft part and that are perpendicular to the longitudinal axis; and an electric control mechanism disposed inside the housing, wherein the electric control mechanism controls the bristle shaft assembly to rotate around the longitudinal axis;
   wherein the head part comprises a substrate, wherein the substrate is equipped with the multiple bristles and disposed around the shaft part;
   wherein the shaft part is connected to a gearbox separately through a connector;
   wherein an O-shaped seal ring is disposed at the end of the bristle shaft; and
   wherein the gearbox is connected to a motor and the motor is connected to a PCB board.

9. The electric toothbrush according to claim 8, wherein the electric control mechanism comprises a direction switch, wherein operating the direction switch can make a direction in which the bristle shaft assembly rotates around the longitudinal axis change from one rotation direction to another opposite rotation direction.

10. The electric toothbrush according to claim 8, wherein the electric control mechanism comprises an activation switch, wherein operating the activation switch can activate or stop rotation of the bristle shaft assembly.

11. The electric toothbrush according to claim 10, wherein operating the activation switch can make a rotation speed of the bristle shaft assembly change from a first rotation speed to a second rotation speed that is higher than the first rotation speed.

12. The electric toothbrush according to claim 8, wherein the multiple bristles are fixed to the substrate by means of ultrasonic welding.

\* \* \* \* \*